US010478515B2

(12) United States Patent
Shur et al.

(10) Patent No.: US 10,478,515 B2
(45) Date of Patent: *Nov. 19, 2019

(54) MULTI WAVE STERILIZATION SYSTEM

(71) Applicant: Sensor Electronic Technology, Inc., Columbia, SC (US)

(72) Inventors: Michael Shur, Latham, NY (US); Maxim S. Shatalov, Columbia, SC (US); Timothy James Bettles, Columbia, SC (US); Yuri Bilenko, Columbia, SC (US); Saulius Smetona, Concord, NC (US); Alexander Dobrinsky, Loudonville, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/622,004

(22) Filed: Jun. 13, 2017

(65) Prior Publication Data

US 2017/0340761 A1  Nov. 30, 2017

Related U.S. Application Data

(63) Continuation of application No. 14/012,652, filed on Aug. 28, 2013, now Pat. No. 9,750,830.

(Continued)

(51) Int. Cl.
*G05D 23/00* (2006.01)
*F25D 3/04* (2006.01)
(Continued)

(52) U.S. Cl.
CPC . *A61L 2/10* (2013.01); *A61L 9/20* (2013.01); *A61L 2202/14* (2013.01); *F25D 3/00* (2013.01); *F25D 3/04* (2013.01); *G05D 23/00* (2013.01)

(58) Field of Classification Search
CPC .. A61L 9/20; A61L 2202/11; A61L 2209/212; A61L 2/0047; F25D 2317/0417;
(Continued)

(56) References Cited

U.S. PATENT DOCUMENTS 2,482,507 A   9/1949  Rentschler et al.
3,817,703 A   6/1974  Atwood
(Continued)

FOREIGN PATENT DOCUMENTS

CN    1269246 A   10/2000
CN    2488020 Y   4/2002
(Continued)

OTHER PUBLICATIONS

Mayekar, K., U.S. Appl. No. 14/629,508, Notice of Allowance, dated Nov. 16, 2017, 22 pages.
(Continued)

*Primary Examiner* — Frantz F Jules
*Assistant Examiner* — Erik Mendoza-Wilkenfel
(74) *Attorney, Agent, or Firm* — LaBatt, LLC

(57) ABSTRACT

Ultraviolet radiation is directed within an area. The target wavelength ranges and/or target intensity ranges of the ultraviolet radiation sources can correspond to at least one of a plurality of selectable operating configurations including a virus destruction operating configuration and a bacteria disinfection operating configuration. Each configuration can include a unique combination of the target wavelength range and target intensity range.

20 Claims, 7 Drawing Sheets

Related U.S. Application Data

(60) Provisional application No. 61/694,235, filed on Aug. 28, 2012.

(51) Int. Cl.
   *F25D 3/00* (2006.01)
   *A61L 9/20* (2006.01)
   *A61L 2/10* (2006.01)

(58) Field of Classification Search
   CPC ... F25D 3/00; F25D 3/04; F25D 3/045; F25D 3/06; F25D 3/08; F24F 2003/1677; G05D 23/00; A23L 3/00; A23L 3/32
   See application file for complete search history.

(56) References Cited

U.S. PATENT DOCUMENTS

| | | |
|---|---|---|
| 4,736,416 A | 4/1988 | Weinert |
| 4,857,277 A | 8/1989 | Broomfield |
| 4,867,052 A | 9/1989 | Cipelletti |
| 5,078,971 A | 1/1992 | Matuda et al. |
| 5,117,642 A | 6/1992 | Nakanishi et al. |
| 5,136,170 A | 8/1992 | Gellert |
| 5,230,220 A | 7/1993 | Kang et al. |
| 5,364,645 A | 11/1994 | Lagunas-Solar et al. |
| 5,454,944 A | 10/1995 | Clack |
| 5,768,898 A | 6/1998 | Seok et al. |
| 5,836,669 A | 11/1998 | Hed |
| 5,865,959 A | 2/1999 | Meinzer et al. |
| 5,889,684 A | 3/1999 | Ben-David et al. |
| 5,901,564 A | 5/1999 | Comeau, II |
| 5,919,422 A | 7/1999 | Yamanaka et al. |
| 6,165,526 A | 12/2000 | Newman |
| 6,182,453 B1 | 2/2001 | Forsberg |
| 6,312,608 B1 | 11/2001 | Buckner |
| 6,447,721 B1 | 9/2002 | Horton, III et al. |
| 6,471,136 B1 | 10/2002 | Chatterjee et al. |
| 6,477,853 B1 | 11/2002 | Khorram |
| 6,524,529 B1 | 2/2003 | Horton, III |
| 6,565,803 B1 | 5/2003 | Bolton et al. |
| 6,574,984 B1 | 6/2003 | McCrea et al. |
| 6,576,188 B1 | 6/2003 | Rose et al. |
| 6,579,495 B1 | 6/2003 | Maiden |
| 6,592,816 B1 | 7/2003 | Ebel et al. |
| 6,673,137 B1 | 1/2004 | Wen |
| 6,735,479 B2 | 5/2004 | Fabian et al. |
| 6,818,177 B1 | 11/2004 | Turcotte |
| 6,878,761 B2 | 4/2005 | Gugumus |
| 7,026,018 B2 | 4/2006 | Kranovich |
| 7,160,370 B2 | 1/2007 | Baca et al. |
| 7,296,422 B2 | 11/2007 | Strohm et al. |
| 7,323,065 B2 | 1/2008 | Fencl et al. |
| 7,401,469 B2 | 7/2008 | Joshi et al. |
| 7,452,561 B2 | 11/2008 | Newman |
| 7,634,996 B2 | 12/2009 | Gaska et al. |
| 7,645,381 B2 | 1/2010 | Oranski et al. |
| 7,754,156 B2 | 7/2010 | Hyde et al. |
| 7,897,104 B2 | 3/2011 | Kwon |
| 8,062,589 B2 | 11/2011 | Naarup |
| 8,114,342 B2 | 2/2012 | Jung et al. |
| 8,178,042 B2 | 5/2012 | Jung et al. |
| 8,277,734 B2 | 10/2012 | Koudymov et al. |
| 8,384,047 B2 | 2/2013 | Shur et al. |
| 8,828,315 B2 | 9/2014 | Ryska et al. |
| 9,006,680 B2 | 4/2015 | Bettles et al. |
| 9,042,967 B2 | 5/2015 | Dacosta et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,878,061 B2 | 1/2018 | Shur et al. |
| 10,172,968 B2 | 1/2019 | Shur et al. |
| 10,383,964 B2 | 8/2019 | Shatalov et al. |
| 2002/0063954 A1 | 5/2002 | Horton, III |
| 2002/0074559 A1 | 6/2002 | Dowling et al. |
| 2002/0122743 A1 | 9/2002 | Huang |
| 2002/0176809 A1 | 11/2002 | Siess |
| 2003/0019222 A1 | 1/2003 | Takahashi et al. |
| 2003/0019505 A1 | 1/2003 | Scheir et al. |
| 2003/0164754 A1 | 9/2003 | Roseen |
| 2003/0194692 A1 | 10/2003 | Purdum |
| 2004/0018125 A1 | 1/2004 | Yang et al. |
| 2004/0210099 A1 | 10/2004 | Shiratori |
| 2005/0165499 A1 | 7/2005 | Stein |
| 2005/0178977 A1 | 8/2005 | Koenck et al. |
| 2005/0186124 A1 | 8/2005 | Fink et al. |
| 2005/0217282 A1 | 10/2005 | Strohm et al. |
| 2005/0257827 A1 | 11/2005 | Gaudiana et al. |
| 2005/0274965 A1 | 12/2005 | Phillips et al. |
| 2006/0091310 A1 | 5/2006 | Furry |
| 2006/0130498 A1 | 6/2006 | Joshi et al. |
| 2006/0147339 A1 | 7/2006 | Hunter et al. |
| 2006/0163169 A1 | 7/2006 | Eckhardt et al. |
| 2006/0216193 A1 | 9/2006 | Johnson et al. |
| 2006/0237687 A1 | 10/2006 | Yue et al. |
| 2007/0051901 A1 | 3/2007 | Hopaluk et al. |
| 2007/0104841 A1 | 5/2007 | Min et al. |
| 2007/0164232 A1 | 7/2007 | Rolleri et al. |
| 2007/0172560 A1 | 7/2007 | Mirtsching et al. |
| 2007/0172661 A1 | 7/2007 | Fechner et al. |
| 2007/0196235 A1 | 8/2007 | Shur et al. |
| 2007/0205382 A1 | 9/2007 | Gaska et al. |
| 2007/0248487 A1 | 10/2007 | Kay et al. |
| 2007/0295203 A1 | 12/2007 | Shekarriz et al. |
| 2008/0061005 A1 | 3/2008 | Hopaluk et al. |
| 2008/0067418 A1 | 3/2008 | Ross |
| 2008/0168788 A1 | 7/2008 | Hurlebaus et al. |
| 2008/0168790 A1 | 7/2008 | Hurlebaus et al. |
| 2008/0213129 A1 | 9/2008 | van der Pol et al. |
| 2008/0286146 A1 | 11/2008 | Schroll et al. |
| 2008/0295033 A1 | 11/2008 | Lee et al. |
| 2008/0307818 A1 | 12/2008 | Min et al. |
| 2009/0110933 A1* | 4/2009 | Hyde ............... A61K 33/00 428/411.1 |
| 2009/0185960 A1 | 7/2009 | Busujima |
| 2009/0228155 A1 | 9/2009 | Slifkin et al. |
| 2009/0229287 A1 | 9/2009 | Prentner |
| 2009/0280035 A1* | 11/2009 | Koudymov ............. A23L 3/28 422/108 |
| 2010/0065632 A1 | 3/2010 | Babcock et al. |
| 2010/0097013 A1 | 4/2010 | Inskeep |
| 2010/0101432 A1 | 4/2010 | Biotti et al. |
| 2010/0227031 A1 | 9/2010 | Vasilenko |
| 2010/0296971 A1 | 11/2010 | Gaska et al. |
| 2010/0307973 A1 | 12/2010 | Grcevic |
| 2011/0030560 A1 | 2/2011 | Bohlen et al. |
| 2011/0044848 A1 | 2/2011 | Wright |
| 2011/0147617 A1 | 6/2011 | Shur et al. |
| 2011/0163046 A1 | 7/2011 | Neal et al. |
| 2011/0228534 A1 | 9/2011 | Zhang et al. |
| 2011/0297241 A1 | 12/2011 | Biotti et al. |
| 2011/0306262 A1 | 12/2011 | Aprin |
| 2012/0011874 A1 | 1/2012 | Conradt et al. |
| 2012/0017628 A1 | 1/2012 | Okabe et al. |
| 2012/0025104 A1* | 2/2012 | Park ..................... A23L 3/28 250/492.1 |
| 2012/0051030 A1 | 3/2012 | Johnson |
| 2012/0085116 A1 | 4/2012 | Maeng et al. |
| 2012/0104021 A1 | 5/2012 | Cur et al. |
| 2012/0126134 A1 | 5/2012 | Deal et al. |
| 2013/0015753 A1 | 1/2013 | Son et al. |
| 2013/0048545 A1 | 2/2013 | Shatalov et al. |
| 2013/0337121 A1 | 12/2013 | Sugano et al. |
| 2014/0042012 A1 | 2/2014 | Clement et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0102127 A1 | 4/2014 | Yum et al. |
| 2014/0202962 A1 | 7/2014 | Bilenko et al. |

(56) References Cited

U.S. PATENT DOCUMENTS

| | | |
|---|---|---|
| 2014/0209928 A1 | 7/2014 | Teng et al. |
| 2015/0008167 A1 | 1/2015 | Shturm et al. |
| 2015/0069270 A1 | 3/2015 | Shur et al. |
| 2015/0161909 A1 | 6/2015 | Won et al. |
| 2015/0165079 A1 | 6/2015 | Shur et al. |
| 2015/0217011 A1 | 8/2015 | Bettles et al. |
| 2015/0297767 A1 | 10/2015 | Gaska et al. |
| 2015/0336810 A1 | 11/2015 | Smetona et al. |
| 2016/0000953 A1 | 1/2016 | Bettles et al. |
| 2016/0058020 A1 | 3/2016 | Shur et al. |
| 2016/0114186 A1 | 4/2016 | Dobrinsky et al. |
| 2016/0128526 A1 | 5/2016 | Dobrinsky et al. |
| 2016/0324996 A1 | 11/2016 | Bilenko et al. |
| 2017/0057842 A1 | 3/2017 | Dobrinsky et al. |
| 2017/0071332 A1 | 3/2017 | Herring et al. |
| 2017/0100494 A1 | 4/2017 | Dobrinsky et al. |
| 2017/0100495 A1 | 4/2017 | Shur et al. |
| 2017/0100496 A1 | 4/2017 | Shur et al. |
| 2017/0157276 A1 | 6/2017 | Dobrinsky et al. |
| 2017/0189711 A1 | 7/2017 | Shur et al. |
| 2017/0197002 A1 | 7/2017 | Dobrinsky et al. |
| 2017/0245527 A1 | 8/2017 | Dobrinsky et al. |
| 2017/0245616 A1 | 8/2017 | Lakios et al. |
| 2017/0281812 A1 | 10/2017 | Dobrinsky et al. |
| 2018/0243458 A1 | 8/2018 | Shatalov et al. |

FOREIGN PATENT DOCUMENTS

| | | |
|---|---|---|
| CN | 1580626 A | 2/2005 |
| CN | 101171938 A | 5/2008 |
| CN | 101322000 A | 12/2008 |
| CN | 102389579 A | 3/2012 |
| CN | 202236462 U | 5/2012 |
| CN | 102564003 A | 7/2012 |
| CN | 103550799 A | 2/2014 |
| EP | 1038536 B1 | 6/2005 |
| JP | 2002204653 A | 7/2002 |
| KR | 1020090074966 A | 7/2009 |
| KR | 1020110057773 A | 6/2011 |
| KR | 1020120011458 A | 2/2012 |
| WO | 2013096243 A1 | 6/2013 |
| WO | 2014036137 A1 | 3/2014 |

OTHER PUBLICATIONS

Li, X., Application No. 201380053801.8, Rejection Decision—with English translation, dated Nov. 6, 2017, 14 pages.
Cheng, X., Application No. 201380053723.1, Notice of Allowance, dated Mar. 3, 2017, 2 pages (no English translation available).
Cheng, X., Application No. 201380053723.1, Office Action1—English translation, dated Jun. 6, 2016, 11 pages.
Zhou, Z., Application No. 201380056459.7, Office Action1 (with English translation), dated Jun. 14, 2017, 13 pages (Jun. 30, 2017).
Zhou, Z., Application No. 201380053729.9, Office Action1 (with English translation), dated Mar. 14, 2017, 21 pages.
Li, X., Application No. 201380053801.8, Office Action2—with English translation, dated Apr. 21, 2017, 16 pages (May 5, 2017).
Li, X., Application No. 201380053801.8, Office Action1—English translation, Jul. 22, 2016, 7 pages.
Kim, International Application No. PCT/US2013/057077, Search Report and Written Opinion, dated Nov. 8, 2013, 10 pages.
Yang, International Application No. PCT/US2013/056997, Search Report and Written Opinion, dated Nov. 28, 2013, 12 pages.
Yang, International Application No. PCT/US2013/056986, Search Report and Written Opinion, dated Nov. 29, 2013, 12 pages.
Yang, International Application No. PCT/US2013/056983, Search Report and Written Opinion, dated Dec. 19, 2013, 12 pages.
Zhou, Z., Application No. 201380053729.9, Office Action2 (with English translation), dated Jan. 29, 2018, 13 pages.
Martin, E., U.S. Appl. No. 15/670,750, Non-Final Rejection, dated Mar. 15, 2018, 62 pages.
Zhou, Z., Application No. 201380056459.7, Notice of Allowance (There is no English translation available.), dated Mar. 13, 2018, 2 pages.
Cox, A., U.S. Appl. No. 14/012,637, Notice of Allowance, dated Jan. 19, 2018, 43 pages.
Stoffa, W., U.S. Appl. No. 15/388,506, Notice of Allowance, dated Sep. 6, 2017, 35 pages.
Mayekar, K., U.S. Appl. No. 15/700,533, Office Action1, dated May 22, 2018, 68 pages.
Zhou, Z., Application No. 201380053729.9, Rejection Devision (with English translation), Jul. 25, 2018, dated Aug. 22, 2018, 13 pages.
Martin, E., U.S. Appl. No. 15/982,611, Non-Final Rejection, dated Aug. 1, 2018, 31 pages.
果品蔬菜保鲜技术和设备 (Google translation of title: "Fruit and vegetable preservation technology and equipment"), Mar. 14, 2017, 2 pages.
Bialka et al., "Decontamination of *Escherichia coli* O157:H7 and *Salmonella enterica* on Blueberries Using Ozone and Pulsed UV-Light," Journal of Food Science, 2007, 7 pages, vol. 72, No. 9.
Bialka et al., "Modeling the inactivation of *Escherichia coli* O157:H7 and *Salmonella enterica* on raspberries and strawberries resulting from exposure to ozone or pulsed UV-light," Journal of Food Engineering, 2008, 6 pages, vol. 85.
Bialka et al., "Pulsed UV-light Penetration of Characterization and the Inactivation of *Escherichia coli* K12 in Solid Model Systems," Abstract, American Society of Agricultural and Biological Engineers, 2013, 1 page.
Bialka et al., "Efficacy of Pulsed UV-Light for the Decontamination of *Escherichia coli* 0157:H7 and *Salmonella* spp. on Raspberries and Strawberries," Journal of Food Science, 2008, 7 pages, vol. 73, No. 5.
Chang et al., "Removal of Ethylene and Secondary Organic Aerosols Using UV-C 254+185 with TiO2 Catalyst," Aerosol and Air Quality Research, 2013, 9 pages.
Cheba et al., "Inactivation of *E. coli* cell viability and DNA Photo-breakage by Pulsed Nitrogen Laser Radiation," American Institute of Physics, 2005, 5 pages.
Chisari et al., "Improving the quality of fresh-cut melon through inactivation of degradative oxidase and pectinase enzymatic activities by UV-C treatment," Institute of Food Science and Technology, 2011, 6 pages.
Demirci et al., "Disinfection of water by flow-through a Pulsed UV Light Sterilization System," Abstract, Ultrapure Water Journal, 2000, 1 page.
Demirci et al., "Pulsed Ultraviolet Light," Sage Publications, 2008, 5 pages.
Hillegas et al., "Inactivation of Clostridium sporogenes in Clover Honey by Pulsed UV-light Treatment," Abstract, American Society of Agricultural and Biological Engineers, 2013, 1 page.
Jun et al., "Pulsed UV-light treatment of corn meal for inactivation of Aspergillus niger spores," International Journal of Food Science and Technology, 2003, 6 pages.
Kennedy et al., "An investigation of the thermal inactivation of *Staphylococcus aurues* and the potential for increased thermotolerance as a result of chilled storage," Journal of Applied Microbiology, 2005, 7 pages.
Krishnamurthy et al., "Inactivation of *Staphylococcus aureus* by Pulsed UV-Light Sterilization," Abstract, Journal of Food Protection, 2004, 1 page.
Krishnamurthy et al., "Inactivation of *Staphylococcus aureus* in Milk and Milk Foam by Pulsed UV-Light Treatment and Su+R170rFace Response Modeling," Abstract, American Society of Agriculutural and Biological Engineers, 2013, 1 page.
Krishnamurthy et al., "Inactivation of *Staphylococcus aureus* in Milk Using Flow-Through Pulsed UV-Light Treatment System," Journal of Food Science, 2007, 7 pages, vol. 72, No. 7.
Krishnamurthy et al., "Microscopic and Spectroscopic Evaluation of Inactivation of *Staphylococcus aureus* by Pulsed UV Light and Infrared Heating," Food Bioprocess Technology, 2010, 12 pages.

(56) References Cited

OTHER PUBLICATIONS

Ozer et al., "Inactivation of *Escherichia coil* O157:H7 and Listeria monocytogenes inoculated on raw salmon fillets by pulsed UV-light treatment," International Journal of Food Science and Technology, 2006, 7 pages.

Sharma et al., "Inactivation of *Escherichia coli* O157:H7 on Inoculated Alfalfa Seed with Pulsed Ultraviolet Light and Response Surface Modeling," Food Microbiology and Safety, 2003, 6 pages.

Zhang et al., "Nonthermal Processing Technologies for Food," Chapters 18 and 19, IFT Press, 2011, 21 pages.

Mayekar, K., U.S. Appl. No. 14/012,682, Non-Final Rejection, dated Sep. 24, 2014, 20 pages.

Mayekar, K., U.S. Appl. No. 14/012,682, Notice of Allowance, dated Jan. 22, 2015, 16 pages.

Mayekar, K., U.S. Appl. No. 14/629,508, Non-Final Rejection, dated Jun. 13, 2017, 74 pages.

Martin, E., U.S. Appl. No. 14/012,667, Notice of Allowance, dated Jun. 16, 2017, 25 pages.

Martin, E., U.S. Appl. No. 14/012,667, Final Rejection2, dated Nov. 30, 2016, 25 pages.

Martin, E., U.S. Appl. No. 14/012,667, Non-Final Rejection, dated Dec. 3, 2015, 73 pages.

Martin, E., U.S. Appl. No. 14/012,667, Final Rejection 1, dated Apr. 1, 2016, 15 pages.

Martin, E., U.S. Appl. No. 14/012,667, Non-Final Rejection2, dated Jun. 28, 2016, 20 pages.

Martin, E., U.S. Appl. No. 14/541,245, Notice of Allowance, dated Apr. 3, 2017, 18 pages.

Martin, E., U.S. Appl. No. 14/541,245, Final Rejection 1, dated Nov. 28, 2016, 23 pages.

Martin, E., U.S. Appl. No. 14/541,245, Non-Final Rejection 1, dated Jun. 17, 2016, 60 pages.

Mendoza-Wilkenfe, E., U.S. Appl. No. 14/012,652, Notice of Allowance, dated Mar. 10, 2017, 37 pages.

Mendoza-Wilkenfe, E., U.S. Appl. No. 14/012,652, Final Rejection, dated Nov. 17, 2016, 22 pages.

Mendoza-Wilkenfe, E., U.S. Appl. No. 14/012,652, Non-Final Rejection, dated Jun. 1, 2016, 74 pages.

Stoffa, W., U.S. Appl. No. 14/012,644, Non-Final Rejection, dated Mar. 10, 2014, 30 pages.

Stoffa, W., U.S. Appl. No. 14/012,644, Final Rejection, dated Jul. 3, 2014, 18 pages.

Stoffa, W., U.S. Appl. No. 14/012,644, Non-Final Rejection, dated Oct. 21, 2014, 19 pages.

Stoffa, W., U.S. Appl. No. 14/012,644, Notice of Allowance, dated Apr. 1, 2015, 15 pages.

Stoffa, W., U.S. Appl. No. 14/012,644, Notice of Allowance, dated Jul. 9, 2015, 32 pages.

Stoffa, W., U.S. Appl. No. 14/937,090, Notice of Allowance, dated Mar. 2, 2017, 18 pages.

Stoffa, W., U.S. Appl. No. 14/937,090, Final Rejection, dated Oct. 27, 2016, 45 pages.

Stoffa, W., U.S. Appl. No. 14/937,090, Non-Final Rejection, dated Jun. 1, 2016, 45 pages.

Stoffa, W., U.S. Appl. No. 15/388,506, Non-Final Rejection, dated Apr. 12, 2017, 51 pages.

Cox, A., U.S. Appl. No. 14/012,637, Final Rejection, dated Feb. 2, 2017, 33 pages.

Cox, A., U.S. Appl. No. 14/012,637, Final Rejection1 (updated to Non-Final Rejection Nov. 18, 2016), dated Aug. 25, 2016, 27 pages.

Cox, A., U.S. Appl. No. 14/012,637, Non-Final Rejection, dated Feb. 19, 2016, 49 pages.

Cox, A., U.S. Appl. No. 14/012,637, Non-Final Rejection, dated Jun. 29, 2017, 35 pages.

Krishnamurthy et al., "Food Processing Operations and Modeling: Design and Analysis," UV Pasteurization of Food Materials, Chapter 11, 2009, 22 pages.

Martin, E., U.S. Appl. No. 15/670,750, Notice of Allowance, dated Aug. 27, 2018, 7 pages.

Martin, E., U.S. Appl. No. 15/982,611, Notice of Allowance, dated Dec. 11, 2018, 11 pages.

Stoffa, W., U.S. Appl. No. 15/856,978, Office Action, dated Sep. 7, 2018, 30 pages.

Mayekar, K., U.S. Appl. No. 15/700,533, Notice of Allowance, dated Sep. 21, 2018, 8 pages.

Mayekar, K., U.S. Appl. No. 15/388,394, Final Office Action, dated Nov. 9, 2018, 7 pages.

Wang, R., Application No. 201510249047.6, Office Action 1, dated Feb. 11, 2019, 11 pages.

Mayekar, K., U.S. Appl. No. 15/388,394, Office Action1, dated Mar. 30, 2018, 81 pages.

Mayekar, K., U.S. Appl. No. 14/012,682, Notice of Allowance 2, dated Apr. 4, 2019, 7 pages.

Stoffa, W., U.S. Appl. No. 15/856,978, Final Office Action 1, dated Apr. 24, 2019, 7 pages.

Mayekar, K., U.S. Appl. No. 15/388,394, Notice of Allowance, dated May 28, 2019, 7 pages.

Stoffa, W. U.S. Appl. No. 15/856,978, Notice of Allowance, dated Aug. 14, 2019, 7 pages.

Mendoza-Wilkenfe, E., U.S. Appl. No. 15/941,413, Office Action 1, dated Aug. 20, 2019, 17 pages.

\* cited by examiner

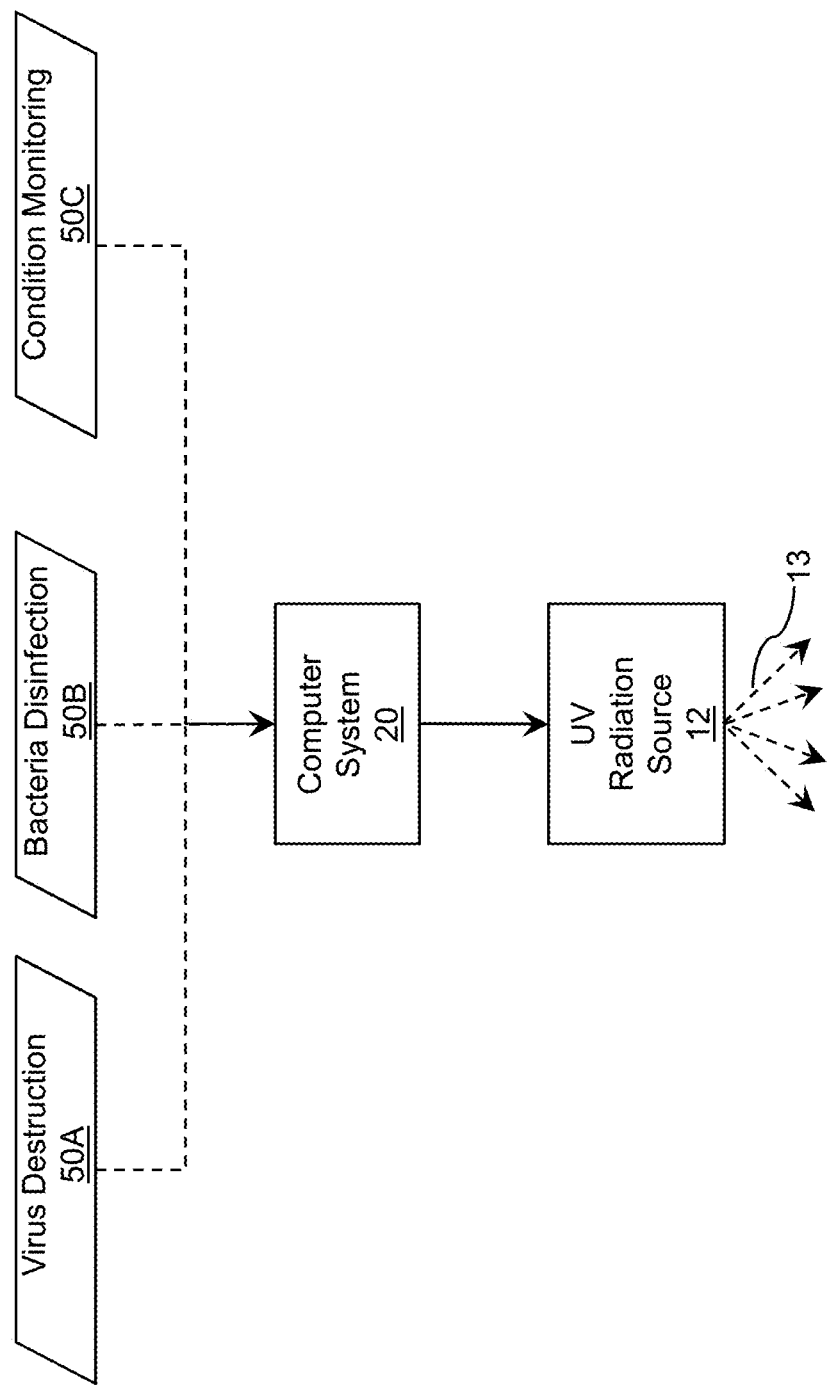

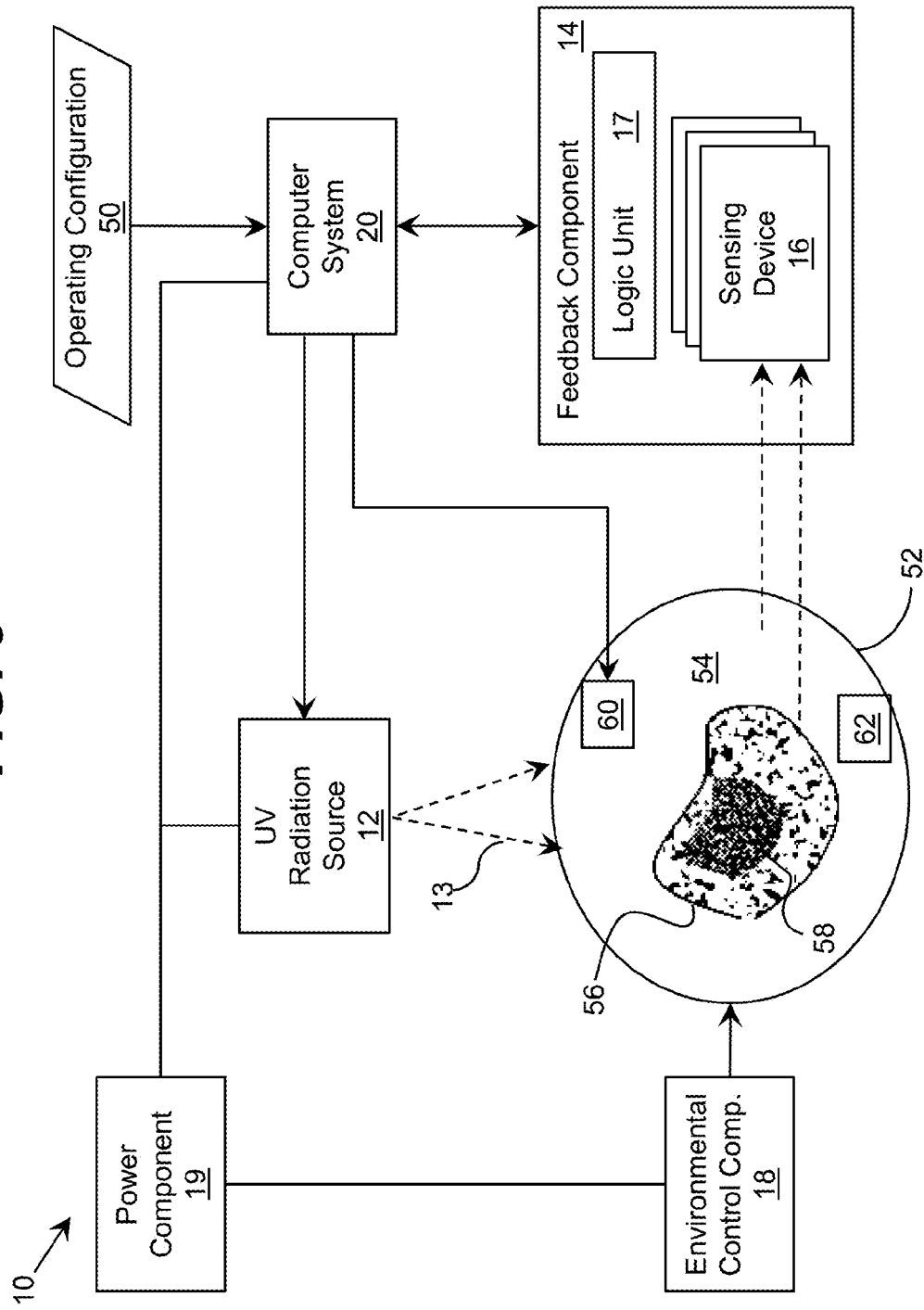

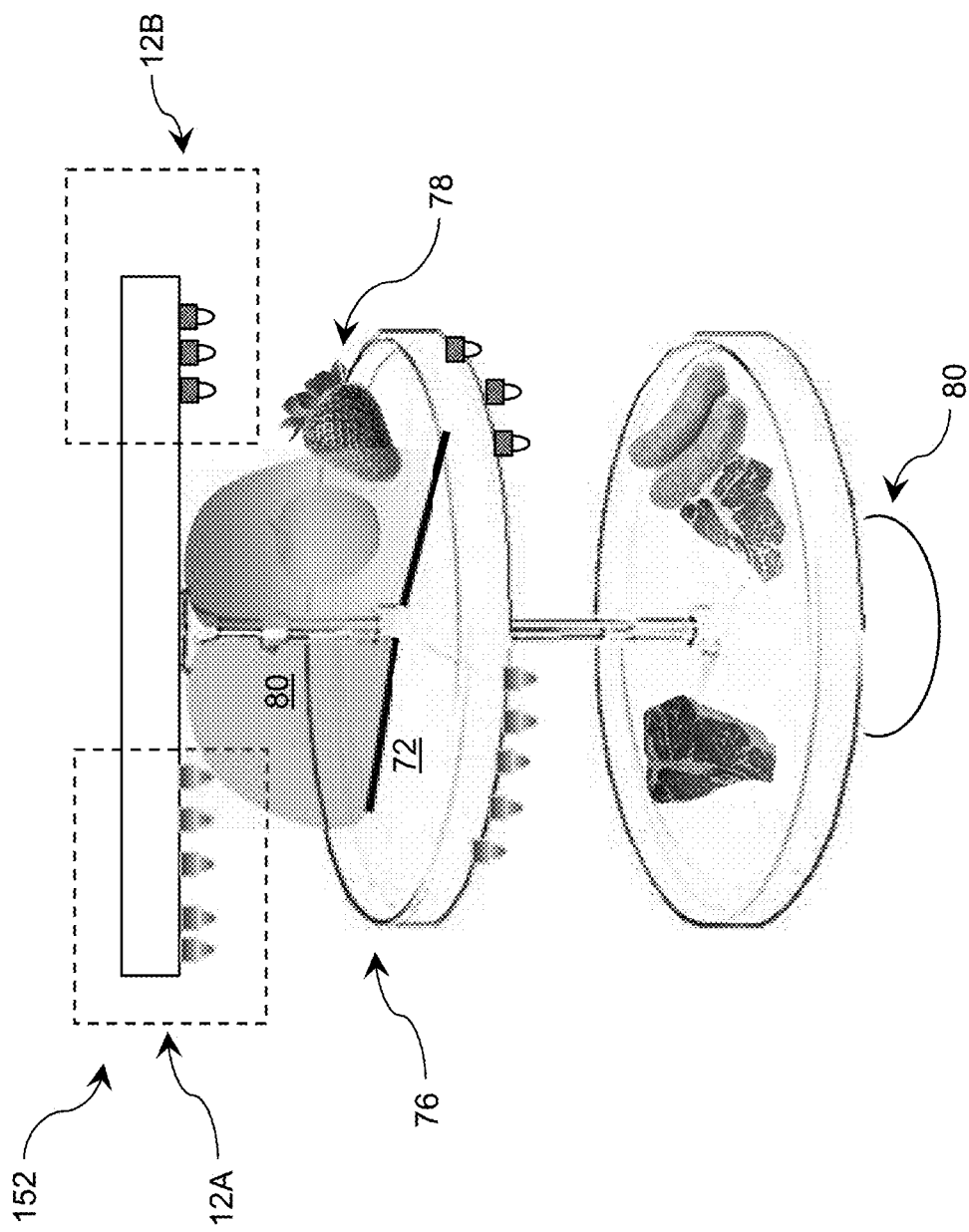

MULTI WAVE STERILIZATION SYSTEM

REFERENCE TO RELATED APPLICATION

The current application is a continuation of U.S. application Ser. No. 14/012,652, filed on 28 Aug. 2013, which claims the benefit of U.S. Provisional Application No. 61/694,235, filed on 28 Aug. 2012, both of which are hereby incorporated by reference.

TECHNICAL FIELD

The disclosure relates generally to ultraviolet radiation, and more particularly, to a solution for using ultraviolet radiation for destroying, suppressing, and/or the like, microorganisms, such as viruses, bacteria, and/or the like, located in a storage area of a storage device.

BACKGROUND ART

Reliable, hygienic storage of sanitary and biological items, such as food, is a major problem. For example, the problem is present throughout the food industry, e.g., manufacturers, retailers, restaurants, and in every household, and is especially significant for food service establishments, in which related issues of food quality control also are significant. In addition to food storage and quality control in fixed locations (e.g., a refrigerator) where access to electricity is readily available, proper food storage and quality control also is important in situations for which access to unlimited electricity and/or a stationary storage device, such as a refrigerator, is not available, such as picnics, camping, mobile food kiosks, hospitality or battlefield meal locations, search and rescue, etc. In addition to food, other stored items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

Fresh food products can be processed using ultraviolet light as a germicidal medium to reduce the food-born microbial load. Water has been treated with ultraviolet light to provide safe drinking water for quite some time. Fruit and vegetable products capable of being pumped through a system generally are very suitable for processing by ultraviolet light to reduce the microbial load. Today, most of these products are pasteurized to obtain microbiologically safe and nutritious products. However, pasteurization can change the taste and flavor of such products because of the temperature and processing time. Juices from different sources can be treated by exposure to ultraviolet light at different doses. On the other hand, variables such as exposure time, type of fruit product, juice color and juice composition, among other variables, need to be studied to obtain fruit products with reduced microbial load, increased shelf life and adequate sensory and nutritional characteristics. Reduction of microbial load through ultraviolet light application as a disinfection medium for food products other than liquids also is being studied. Moreover, ultraviolet technology could be a source for pasteurization of liquids, or disinfection of solid foods as an alternative technology, instead of thermal treatment or application of antimicrobial compounds.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

A microbicidal ultraviolet (UV) radiation fluence (e.g., dosage) is typically measured using the DNA absorbance spectrum as a weighting factor for the relevant wavelength effectiveness. However, this DNA-based weighting does not necessarily match the spectral sensitivity of the microorganism being treated. For example, *Bacillus subtilis* spores are often used for UV reactor validation in Europe. Conversely, MS2 coliphage is typically used for validation testing in the United States. When both these organisms were exposed to quasimonochromatic UV radiation across the microbicidal spectrum from approximately 214 nm to approximately 293 nm, MS2 was three times more sensitive to wavelengths near approximately 214 nm, whereas *Bacillus subtilis* spores were more sensitive to wavelengths at approximately 256 nm.

SUMMARY OF THE INVENTION

The inventors provide a solution for using ultraviolet radiation for destroying, suppressing, and/or the like, microorganisms, such as viruses, bacteria, and/or the like, located in a storage area of a storage device, such as a storage area of a refrigerated unit. For example, an embodiment of the solution is configured to apply a target intensity and wavelength of ultraviolet radiation to preserve and/or disinfect the storage area by destroying and/or suppressing the reproductive function of viruses and/or bacteria, which may be located within the storage area. Similarly, this solution may be implemented as part of other storage environments, such as pantries, grocery bags, boxes, biological object storage containers, and/or the like.

Aspects of the invention provide a solution in which ultraviolet radiation is directed within an area. The target wavelength ranges and target intensity ranges of the ultraviolet radiation sources can correspond to at least one of a plurality of selectable operating configurations including a virus destruction operating configuration and a bacteria disinfection operating configuration. Each operating configuration can have a unique combination of a target ultraviolet wavelength and a target ultraviolet intensity.

A first aspect of the invention provides a system comprising: at least one ultraviolet radiation source configured to generate ultraviolet radiation directed within an area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a virus destruction operating configuration, and a bacteria disinfection operating configuration.

A second aspect of the invention provides a food storage device comprising: a storage area configured to store at least one perishable food item; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a virus destruction operating configuration, and a bacteria disinfection operating configuration.

A third aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a virus destruction operating configuration, and a bacteria disinfection operating configuration.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 2 shows a block diagram illustrating use of operating configurations for operating an ultraviolet radiation source according to an embodiment.

FIG. 3 shows an illustrative system including an ultraviolet radiation system according to an embodiment.

FIG. 7 shows a perspective view of an illustrative storage device according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which ultraviolet radiation is directed within an area. The target wavelength ranges and target intensity ranges of the ultraviolet radiation sources correspond to at least one of a plurality of selectable operating configurations including a virus destruction operating configuration, and a bacteria disinfection operating configuration. As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through.

Figure 1:
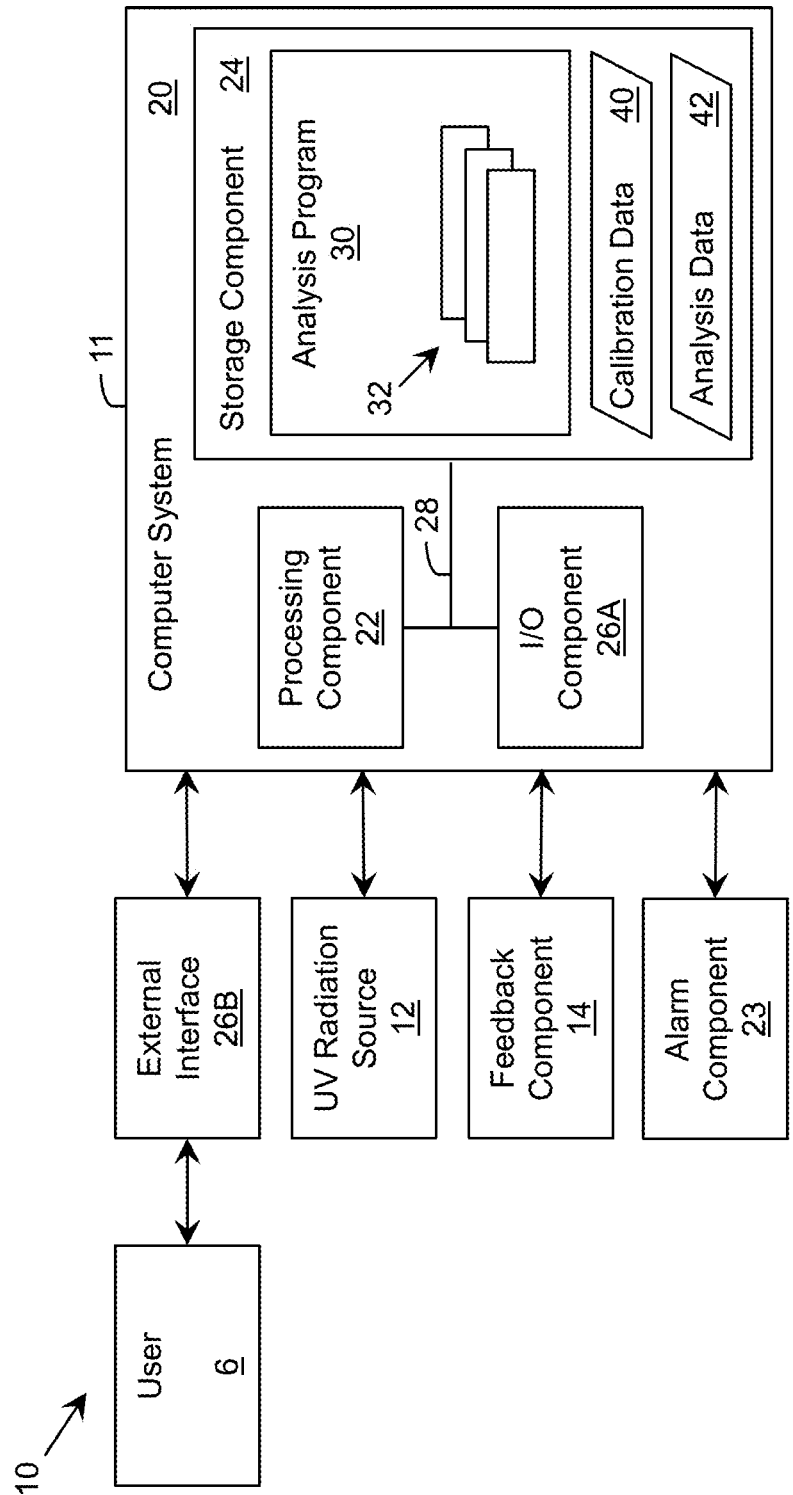
FIG. 1 shows an illustrative ultraviolet radiation system according to an embodiment.

Turning to the drawings, FIG. 1 shows an illustrative ultraviolet radiation system 10 according to an embodiment. In this case, the system 10 includes a monitoring and/or control system 11, which is implemented as a computer system 20 including an analysis program 30, which makes the computer system 20 operable to manage an ultraviolet (UV) radiation source 12 by performing a process described herein. In particular, the analysis program 30 can enable the computer system 20 to operate the UV radiation source 12 to generate and direct ultraviolet radiation within an area and process data corresponding to one or more conditions of the area and/or an item located in the area, which is acquired by a feedback component 14. While a single UV radiation source 12 is shown, it is understood that the area can include any number of UV radiation sources 12, the operation of which the computer system 20 can separately manage using a process described herein.

In an embodiment, during an initial period of operation (e.g., after recent access to the area, addition/removal/reconfiguration of item(s) placed within the area, and/or the like), the computer system 20 can acquire data from the feedback component 14 regarding one or more attributes of the items in the area and/or conditions of the area and generate analysis data 42 for further processing. The analysis data 42 can include information on the color, appearance, and/or the like, of items in the area, the presence of microorganisms on the items or within the area, and/or the like. Furthermore, the analysis data 42 can include information on the presence of ethylene gas within the area. The computer system 20 can use the analysis data 42 to generate calibration data 40 for controlling one or more aspects of the ultraviolet radiation generated by the ultraviolet radiation source(s) 12 using one of a plurality of selectable operating configurations as discussed herein. Furthermore, one or more aspects of the operation of the ultraviolet radiation source 12 can be controlled by a user 6 via an external interface component 26B.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 6 to interact with the computer system 20 and/or one or more communications devices to enable a system user 6 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 6 to interact with the analysis program 30. Furthermore, the analysis program 30 can manage (e.g., store, retrieve, create, manipulate, organize, present, etc.) the data, such as calibration data 40 and analysis data 42, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 11 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 11.

Regardless, when the computer system 20 includes multiple computing devices, the computing devices can communicate over any type of communications link. Furthermore, while performing a process described herein, the computer system 20 can communicate with one or more other computer systems, such as the user 6, using any type of communications link. In either case, the communications link can comprise any combination of various types of wired and/or wireless links; comprise any combination of one or more types of networks; and/or utilize any combination of various types of transmission techniques and protocols. This communications link, which can include a wireless or cable based transmission, can be utilized to transmit information about the state of one or more items and/or zones within the storage area 54.

The system 10 can be implemented within an existing storage device (e.g., a refrigerator) using any solution. For example, one or more ultraviolet radiation sources 12 and one or more devices included in a feedback component 14 can be fixed within various locations in the storage device (e.g., on walls, shelves, etc.) and configured for operation by the computer system 20. The locations of devices in the ultraviolet radiation source(s) 12 and/or the feedback component 14 can be selected to provide comprehensive coverage of the storage area of the storage device and the items located within the storage area. In an embodiment, the computer system 20 can be located outside of the storage area of the storage device.

The ultraviolet radiation source 12 can comprise any combination of one or more ultraviolet radiation emitters. For example, the UV source 12 can include a high intensity ultraviolet lamp (e.g., a high intensity mercury lamp), an ultraviolet light emitting diode (LED), and/or the like. In an embodiment, the UV source 12 includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the UV source 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the storage area. Illustrative wave guiding structures include, but are not limited to, a plurality of ultraviolet fibers, each of which terminates at an opening, a diffuser, and/or the like. The computer system 12 can independently control each UV source 12.

The system 10 also can include an alarm component 23, which can be operated by the computer system 20 to indicate when ultraviolet radiation is being directed within the storage area. The alarm component 23 can include one or more devices for generating a visual signal, an auditory signal, and/or the like. For example, in the example shown in FIG. 4A, where the storage device 52 includes a refrigeration device, a panel 8 can display a flashing light, text, an image, and/or the like, to indicate that ultraviolet radiation is currently being directed into a corresponding storage area 54. Furthermore, the alarm component 23 can generate a noise, such as a bell, a beep, and/or the like, to indicate that ultraviolet radiation is currently being directed to the storage area 54.

FIG. 2 shows a block diagram illustrating use of operating configurations for operating an ultraviolet radiation source 12 according to an embodiment. As illustrated, the computer system 20 can use data corresponding to a selected operating configuration 50A-50C to adjust one or more aspects of the ultraviolet radiation 13 generated by the ultraviolet radiation source(s) 12. In an embodiment, the operating configurations 50A-50C include a virus destruction operating configuration 50A, a bacteria disinfection operating configuration 50B, and a condition monitoring operating configuration 50C. In an embodiment, the virus destruction operating configuration 50A is configured to destroy and/or suppress the reproductive function of viruses, while the bacteria disinfection operating configuration 50B is configured to destroy and/or suppress the reproductive function of bacteria and/or larger microorganisms, as discussed herein. While shown as two distinct operating configurations, it is understood that the computer system 20 can operate the ultraviolet radiation source 12 in both operating configurations 50A-50B in order to concurrently harm both viruses as well as bacteria and other microorganisms. Additionally, the computer system 20 can operate the ultraviolet radiation source 12 in a condition monitoring operating configuration 50C, during which a relatively low level of ultraviolet radiation can be generated in order to detect bacteria and/or the like, which may fluoresce in the ultraviolet light.

The computer system 20 is configured to control and adjust a direction, an intensity, a pattern, and/or a spectral power (e.g., wavelength) of the UV sources 12 to correspond to a particular operating configuration 50A-50C. The computer system 20 can control and adjust each property of the UV source 12 independently. For example, the computer system 20 can adjust the intensity, the time duration, and/or the time scheduling (e.g., the pattern) of the UV source 12 for a given wavelength. Each operating configuration 50A-50C can designate a unique combination of: a target ultraviolet wavelength, a target intensity level, a target pattern for the ultraviolet radiation (e.g., time scheduling, including duration (e.g., exposure/illumination time), duty cycle, time between exposures/illuminations, and/or the like), a target spectral power, and/or the like, in order to meet a unique set of goals corresponding to each operating configuration 50A-50C.

For the virus destruction operating configuration 50A, a target wavelength range can be approximately 190 nanometers to approximately 265 nanometers. In more particular embodiment, the wavelength range may be 240 nanometers to 265 nanometers. High intensity radiation can be utilized to sterilize and/or destroy viruses. For example, the intensity for the virus destruction operating configuration 50A can be greater than or equal to approximately 20 mJ/cm$^2$ to obtain a 4 log reduction for many types of viruses. For the bacteria disinfection operating configuration 50B, a target wavelength range can be approximately 260 nanometers to approximately 300 nanometers. In one more particular embodiment, the wavelength range may be 270 nanometers to 300 nanometers. A lower intensity radiation (as compared to the intensity used to kill viruses) can be used to sterilize and/or destroy bacteria and other larger microorganisms. For example, the intensity for the bacteria disinfection operating configuration 40B can be in a range between approximately 5 and approximately 15 mJ/cm$^2$ to obtain a 4 log reduction for many types of bacteria. The ultraviolet radiation for the sterilization and/or destruction of viruses in the virus destruction operating configuration 50A can be continuous. Conversely, the ultraviolet radiation for the sterilization and destruction of bacteria and/or larger microorganisms in the bacteria disinfection operating configuration 50B can include intermittent pulses. The pulses can be configured to provide a target amount of intensity over a target amount of time to sterilize and/or destroy bacteria and/or lager microorganisms that are present.

FIG. 3 shows an illustrative system including an ultraviolet radiation system 10 according to an embodiment. The computer system 20 is configured to control the UV source 12 to direct ultraviolet radiation 13 into a storage area 54 of a storage device 52, within which a set of items 56 are located over a period of time. The feedback component 14 is configured to acquire data used to monitor a set of current conditions of the storage area 54 and/or the items 56 over a period of time. As illustrated, the feedback component 14 can include a plurality of sensing devices 16, each of which can acquire data used by the computer system 20 to monitor the set of current conditions.

It is understood that the set of current conditions in the storage area 54 can include one or more attributes corresponding to a set of biological activity dynamics present within the storage area. The set of biological activity dynamics can include, for example, a presence of biological activity (e.g., exponential bacterial growth), a location of the biological activity, a type of biological activity (e.g., type of organism), a concentration of the biological activity, an estimated amount of time an organism has been in a growth phase (e.g., exponential growth and/or stationary), and/or the like. The set of biological activity dynamics can include information on the variation of the biological activity over time, such as a growth rate, a rate with which an area including the biological activity is spreading, and/or the like. In an embodiment, the set of biological activity dynamics are related to various attributes of bacteria and/or virus activity within an area, including, for example, the presence of detectable bacteria and/or virus activity, measured bacteria and/or virus population/concentration time dynamics, growth phase, and/or the like.

In an embodiment, the sensing devices 16 include at least one of a visual camera or a chemical sensor. The visual camera can acquire data (e.g., visual, electronic, and/or the like) used to monitor the storage area 54 and/or one or more of the items 56 located therein, while the chemical sensor can acquire data (e.g., chemical, electronic, and/or the like) used to monitor the storage area 54 and/or one or more of the items 56 located therein. The set of current conditions of the storage area 54 and/or items 56 can include the color or visual appearance of the items 56, the presence of microorganisms within the storage area 54, and/or the like. In an embodiment, the visual camera comprises a fluorescent optical camera. In this case, when the computer system 20 is operating the UV radiation source 12, a visual camera and/or a chemical sensor monitoring the storage area 54 may be operated to detect the presence of microorganisms as they fluoresce in the ultraviolet light. In an embodiment, the chemical sensor is an infrared sensor, which is capable of detecting any combination of one or more gases, such as ethylene, ethylene oxide, and/or the like. However, it is understood that a visual camera and a chemical sensor are only illustrative of various types of sensors that can be implemented. For example, the sensing devices 16 can include one or more mechanical sensors (including piezoelectric sensors, various membranes, cantilevers, a microelectromechanical sensor or MEMS, a nanomechanical sensor, and/or the like), which can be configured to acquire any of various types of data regarding the storage area 54 and/or items 56 located therein. In another embodiment, the sensing devices 16 can include a UV detector that is configured to detect ultraviolet radiation within the storage area 54. The absorption of ultraviolet radiation within storage area 54 can indicate the presence of bacteria 56 and/or virus 58. The UV detector can be a solid state ultraviolet radiation detector manufactured with one or more layers of materials selected from the group-III nitride material system (e.g., $Al_xIn_yGa_{1-x-y}N$, where $0 \leq X$, $Y \leq 1$, and $X+Y \leq 1$ and/or alloys thereof). For example, the UV detector can comprise any type of ultraviolet sensing device, such as an ultraviolet-sensitive photodetector (e.g., an ultraviolet photodiode). In an embodiment, the UV detector can be selected based on its sensitivity to a particular, narrow band of ultraviolet light, which can be selected using any solution. Additionally, the UV detector can comprise one or more additional components (e.g., a wave guiding structure, filter, system for moving and/or redirecting ultraviolet detector(s), etc.) to detect ultraviolet radiation in a particular location/direction, and make the UV detector sensitive to a particular range of wavelengths, and/or the like.

The feedback component 14 also can include one or more additional devices. For example, the feedback component 14 is shown including a logic unit 17. In an embodiment, the logic unit 17 receives data from a set of sensing devices 16 and provides data corresponding to the set of conditions of the storage area 54 and/or items 56 located in the storage area 54 for processing by the computer system 20. In a more particular embodiment, the computer system 20 can provide information corresponding to the currently selected operating configuration 50 for use by the feedback component 14. For example, the logic unit 17 can adjust the operation of one or more of the sensing devices 16, operate a unique subset of the sensing devices 16, and/or the like, according to the currently selected operating configuration 50. In response to data received from the feedback component 14, the computer system 20 can automatically adjust and control one or more aspects of the ultraviolet radiation 13 generated by the ultraviolet radiation source 12 according to the currently selected operating configuration 50.

In each of the operating configurations 50A, 50B, the target wavelengths and target intensities are designated to destroy and/or damage DNA and RNA molecules of the corresponding microorganism, e.g., virus or bacteria. A DNA molecule and/or RNA molecule of the corresponding microorganisms can absorb a sufficient amount of ultraviolet radiation, at a target wavelength and intensity, which destroys the DNA and/or RNA molecule. This can prevent the reproduction process of the corresponding microorganism. In response to an indication of the presence of biological activity (e.g., the presence of bacteria and/or virus), the computer system 20 can operate UV sources 12 to generate a suppressing dose of ultraviolet radiation of a sufficient amount and at a target wavelength and intensity corresponding to an appropriate operating configuration. 50A, 50B to harm DNA and/or RNA of the detected microorganism. In this manner, UV source 12 also can be used to suppress an amount of organism activity.

Figure 4B:
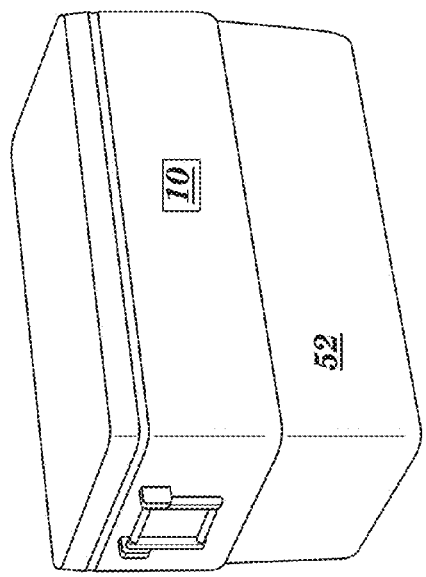
FIGS. 4A-4C show illustrative storage devices for use with an ultraviolet radiation system according to embodiments.
Figure 4C:
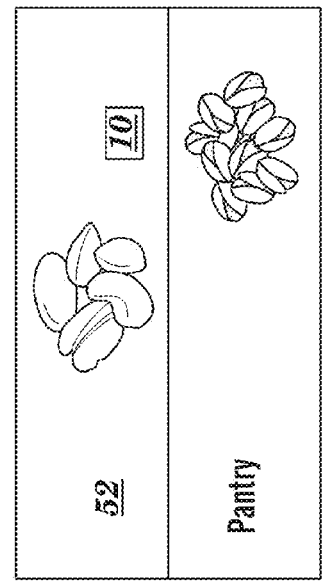
Figure 4A:
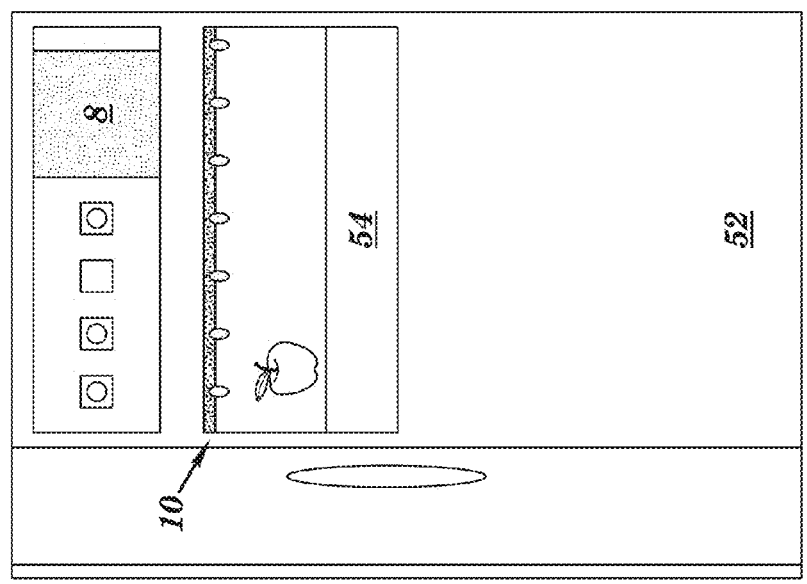
Figure 5A:
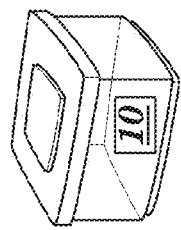
FIGS. 5A-5F show illustrative storage devices for use with an ultraviolet radiation system according to embodiments.
Figure 5B:
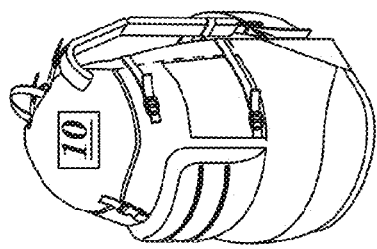
Figure 5C:
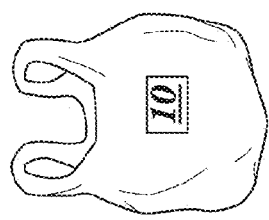
Figure 5D:
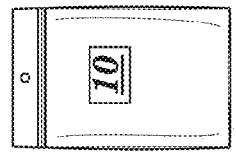
Figure 5E:
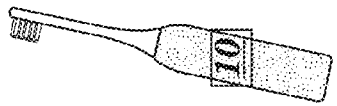
Figure 5F:
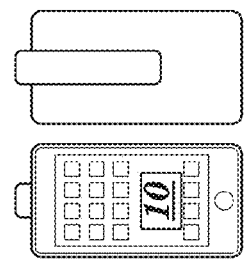
Figure 6B:
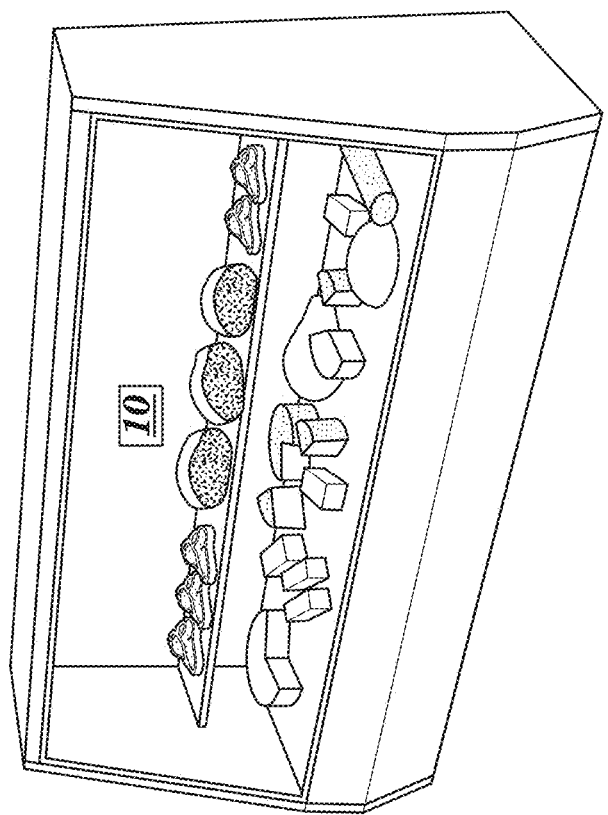
FIGS. 6A and 6B show illustrative storage devices for use with an ultraviolet radiation system according to embodiments.
Figure 6A:
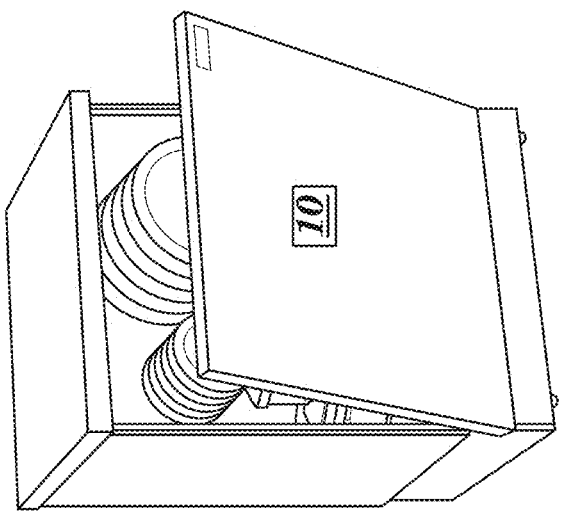

As described herein, embodiments can be implemented as part of any of various types of storage systems. FIGS. 4A-4C, 5A-5F, and 6A-6B show illustrative storage devices for use with an ultraviolet radiation system 10 (FIG. 1) according to embodiments. For example, the storage device can be a refrigerator and/or freezer (FIG. 4A) for storing a plurality of food items. In this embodiment, the computer system 20 can be configured to turn off UV source 12 when a door is open, and automatically turn on UV source 12 when the door is closed. Alternatively, the storage device can be a cooler (FIG. 4B). The storage device can be a pantry (FIG. 4C, e.g., a shelf in the pantry), and/or the like. The storage device can be a food storage container (FIG. 5A), a backpack (FIG. 5B), a grocery bag (FIG. 5C), a plastic baggie (FIG. 5D). In an alternative embodiment, system 10 may be utilized with an electronic toothbrush (FIG. 5E) or with a mobile touch screen phone (FIG. 5F). The storage device can also be a dishwasher (FIG. 6A), or a sushi bar (FIG. 6B). In each case, an embodiment of the system 10 can be implemented in conjunction therewith using any solution. To this extent, it is understood that embodiments of the system 10 can vary significantly in the number of devices, the size of the devices, the power requirements for the system, and/or the like. Regardless, it is understood that these are only exemplary storage devices and that the system 10 may be applicable to other storage devices not specifically mentioned herein.

FIG. 7 shows a perspective view of an illustrative storage device 152 according to an embodiment. In this embodiment, the storage device 152 can include a plurality of sub-compartments that are individually/separately monitored by the computer system 20 (FIG. 1) using the feedback component 14 (FIG. 1). The ultraviolet radiation sources 12 in each sub-compartment can be individually controlled by the computer system 20. For example, a shelf 72 can be partitioned into a first sub-compartment 76 and a second sub-compartment 78, which are separated by a divider 80. Each of the plurality of sub-compartments 76, 78 can include the same type of UV sources 12. Alternatively, as shown in FIG. 7, the first sub-compartment 76 can include a first type of UV source 12A, and the second sub-compartment 78 can include a second type of UV source 12B. In a more specific embodiment, a first UV source 12A can be configured to kill microorganisms, while a second UV source 12B can be configured to suppress the reproduction of microorganisms. The computer system 20 can control the UV sources 12A, 12B, such that the first sub-compartment 76 is subjected to a first operating configuration and the second sub-compartment 78 is subjected to a second operating configuration. The particular operating configuration for each sub-compartment can differ. Furthermore, the computer system 20 can control the UV source 12A to have a first intensity and a first wavelength, and control the UV source 12B to have a second intensity and a second wavelength. For example, the UV source 12A can include a full intensity, while the UV source 12B includes a zero intensity. Conversely, the UV source 12A can include a zero intensity, while the UV source 12B includes a full intensity. Furthermore, the computer system 20 can independently tune the relative intensities of each UV source 12A, 12B, and either UV source 12A, 12B can have any intensity between zero and full.

Returning to FIG. 3, it is understood that the system 10 may include a power component 19 that is implemented separately from the storage device 52 to supply power to one or more of the various components of system 10, such as ultraviolet radiation sources 12, motor 80 (FIG. 10), feedback component 14, computer system 20, and/or the like. For example, the storage device 52 may comprise a cooler or the like, which does not include or otherwise require any power source. Furthermore, the storage device 52 may comprise a power source that is insufficient to operate the various devices of system 10 in addition to maintaining one or more aspects of the environment within the storage area 54 for a desired period of time. Regardless, the power component 19 can be utilized to operate system 10. The power component 19 can comprise any source of power including, but not limited to, the power grid, a battery set, an automotive charger, a solar cell, and/or the like. In an embodiment, the computer system 20 can implement multiple modes of operation depending on the source of power. In particular, when a power component 19 of limited capacity is being utilized, one or more functions of system 10 can be disabled and/or reduced to lengthen an operating time for system 10. For example, use of ultraviolet radiation source 12 to prolong the life of items within the storage area 54 or disinfect the storage area 54 by generating a higher intensity of ultraviolet radiation can be disabled.

An environment within the storage area 54 can be controlled by an environmental control component 18. In an illustrative implementation, the environmental control component 18 can comprise a temperature control module, a humidity control module, and/or a convection control module. During normal operation of the environmental control component 18, a user 6 (FIG. 1) (e.g., using external interface component 26B) can select a desired temperature, humidity, and/or the like, to maintain within storage area 54. The environmental control component 18 can subsequently operate one or more cooling/heating components of temperature control module to maintain the desired temperature, operate one or more humidifying/dehumidifying components of humidity control module to maintain the desired humidity, operate one or more air or fluid convection components (e.g., fan, pump, vent, valve, etc.) of convection control module to assist in maintaining a relatively even temperature/humidity within storage area 54, and/or the like. Alternatively, local temperature control within storage area 54 can be maintained by cool air recirculation that is controlled by the environmental control component 18.

The computer system 20 can be configured to adjust one or more operating parameters of the environmental control component 18 based on a set of current conditions in the storage area 54 and/or an operating configuration of the UV radiation source 12. For example, the computer system 20 can adjust one or more of: a temperature, a humidity, a gas convection, and/or a fluid convection of the storage area 54 in response to a set of biological activity dynamics and according to a currently selected operating configuration. To this extent, each operating configuration can further define a set of target environmental conditions for use during the UV illumination. Such environmental conditions can include a target temperature, a target humidity, additional illumination by non-ultraviolet sources (e.g., visible, infrared), air circulation, and/or the like. Furthermore, one or more of the environmental conditions can change over time during implementation of the operating configuration. In an illustrative embodiment, the computer system 20 can operate the environmental control component 18 to circulate air into a chamber 60. The chamber 60 may be a source of ethylene or other gas and the computer system 20 can control chamber 60 to calibrate exposure of stored articles to such gas. The storage area 52 can also include catalysts for enhancing the suppression of the biological activity, such as, titanium dioxide. Furthermore, the set of current conditions in the storage area 54 can include an operating condition of one or more components of the system 10, such as the ultraviolet radiation source(s) 12. Information regarding the operating condition can be used to, for example, notify a user 6 of a problem using the alarm component 23, alter one or more aspects of an operating configuration, and/or the like. Additionally, the set of current conditions in the storage area 54 can include data corresponding to a dose of ultraviolet radiation delivered by an ultraviolet radiation source 12 during a predetermined time period. In this case, the computer system 20 can dynamically determine when to turn off the ultraviolet radiation source 12.

As described herein, aspects of the invention can be implemented to treat (e.g., preserve, disinfect, and/or the like) various types of food stored in various types of environments. A typical environment can comprise a refrigerated environment, in which food is frequently stored to extend the shelf life of the food. However, embodiments can be implemented in other non-refrigerated environments, in which food is stored for a period of time, e.g., to ripen, prior to being used, and/or the like. Furthermore, an embodiment can be implemented in conjunction with a freezer, in which the temperature is maintained well below the freezing point of water. To this extent, the types of food items to which aspects of the invention can be implemented can include various types of food as described herein. As described herein, the foods can include various types of fruits and vegetables. However, the foods also can include frozen consumables, such as ice cubes, ice cream, and/or the like. Furthermore, the foods can include liquids, grains, cereals, and/or the like. Additionally, as described herein, embodiments can be implemented to treat non-food items stored in any type of environment. Such non-food items can include, for example, frozen/liquid chemicals, sand, wood, and/or the like. Regardless, it is understood that a treated item can be ultraviolet transparent (e.g., semi-transparent), ultraviolet absorbing, and/or ultraviolet reflective.

While shown and described herein as a method and system for managing a storage area, it is understood that aspects of the invention further provide various alternative embodiments. For example, in one embodiment, the invention provides a computer program fixed in at least one computer-readable medium, which when executed, enables a computer system to manage the storage area using a process described herein. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing the storage area. In this case, the generating can include configuring a computer system, such as the computer system 20 (FIG. 1), to implement a method of managing the storage area as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    a set of ultraviolet radiation sources configured to generate ultraviolet radiation directed within a storage area; and
    a monitoring and control system for managing the storage area by performing a method comprising:
        enabling selection of each of a plurality of selectable operating configurations, the plurality of selectable operating configurations including: a virus destruction operating configuration, a bacteria disinfection operating configuration, and a condition monitoring operating configuration, wherein each operating configuration includes a unique combination of a target wavelength, a target intensity range, and a target pattern for the ultraviolet radiation;
        monitoring a set of current conditions of at least one of: the storage area or a set of items located in the storage area, wherein the set of current conditions includes a visual appearance of the at least one of: the storage area or the set of items located in the storage area; and
        controlling ultraviolet radiation generated by the set of ultraviolet radiation sources using a selected one of the plurality of selectable operating configurations and the set of current conditions.

2. The system of claim 1, further comprising at least one of: a visual camera or a chemical sensor for acquiring data used in monitoring the set of current conditions.

3. The system of claim 1, wherein a target intensity range of the ultraviolet radiation in the condition monitoring operating configuration is lower than both: a target intensity range of the ultraviolet radiation in the virus destruction operating configuration and a target intensity range of the ultraviolet radiation in the bacteria disinfection operating configuration.

4. The system of claim 3, wherein the target intensity range of the virus destruction operating configuration is higher than the target intensity range of the ultraviolet radiation in the bacteria disinfection operating configuration.

5. The system of claim 1, wherein the set of ultraviolet radiation sources includes a first ultraviolet radiation source and a second ultraviolet radiation source configured to emit ultraviolet radiation of different peak wavelengths.

6. The system of claim 5, wherein the monitoring and control system is configured to independently control the first ultraviolet radiation source and the second ultraviolet radiation source.

7. The system of claim 1, further comprising an ultraviolet radiation detector configured to detect a level of ultraviolet radiation within the storage area, wherein the monitoring and control system processes data corresponding to the level of ultraviolet radiation to determine a presence of at least one of: bacteria or a virus.

8. The system of claim 1, wherein at least one ultraviolet radiation source in the set of ultraviolet radiation sources is configured to generate ultraviolet radiation to excite a fluorescence, wherein the monitoring and control system processes data corresponding to a level of fluorescence to determine a presence of at least one of: bacteria or microorganisms.

9. The system of claim 1, further comprising a catalyst located within the storage area configured to enhance a suppression of biological activity.

10. A storage device comprising:
    a storage area configured to store at least one item;
    a set of ultraviolet radiation sources configured to generate ultraviolet radiation directed within the storage area; and
    a monitoring and control system for managing the storage area by performing a method comprising:
        enabling selection of each of a plurality of selectable operating configurations, the plurality of selectable operating configurations including: a virus destruction operating configuration, a bacteria disinfection operating configuration, and a condition monitoring operating configuration, wherein each operating configuration includes a unique combination of a target wavelength, a target intensity range, and a target pattern for the ultraviolet radiation;
        monitoring a set of current conditions of at least one of: the storage area or a set of items located in the storage area, wherein the set of current conditions includes a visual appearance of at least one of: the storage area or the set of items located in the storage area; and
        controlling ultraviolet radiation generated by the set of ultraviolet radiation sources using a selected one of the plurality of selectable operating configurations and the set of current conditions.

11. The storage device of claim 10, further comprising at least one of: a visual camera or a chemical sensor for acquiring data used in monitoring the set of current conditions.

12. The storage device of claim 10, wherein the set of current conditions further includes: a presence of biological activity, a location of the biological activity, a determination of a type of the biological activity, and a concentration of the biological activity.

13. The storage device of claim 10, wherein the monitoring further includes analyzing the set of current conditions over a period of time, such that the set of current conditions includes an estimated amount of time an organism has been in a growth phase, a growth rate of biological activity, and a rate with which an area including the biological activity is spreading.

14. The storage device of claim 10, further comprising a set of ultraviolet radiation detectors configured to detect a level of ultraviolet radiation within the storage area, wherein the monitoring and control system processes data corresponding to the level of ultraviolet radiation to determine a presence of at least one of: bacteria or a virus.

15. The storage device of claim 14, wherein the set of ultraviolet radiation detector includes at least one ultraviolet photodiode and the set of ultraviolet radiation sources includes at least one ultraviolet light emitting diode.

16. The storage device of claim 10, wherein at least one ultraviolet radiation source in the set of ultraviolet radiation sources is configured to generate ultraviolet radiation to excite a fluorescence, wherein the monitoring and control system processes data corresponding to a level of fluorescence to determine a presence of at least one of: bacteria or microorganisms.

17. The storage device of claim 10, further comprising a catalyst located within the storage area configured to enhance a suppression of biological activity.

18. A refrigeration device comprising:
    a storage area configured to store at least one refrigerated item;
    a component configured to control at least one environmental condition of the storage area, wherein the at least one environmental condition includes at least one of: a temperature, a humidity, a gas convection, or a fluid convection;
    a set of ultraviolet radiation sources configured to generate ultraviolet radiation directed within the storage area; and
    a monitoring and control system for managing the storage area by performing a method comprising:
        enabling selection of each of a plurality of selectable operating configurations, the plurality of selectable operating configurations including: a virus destruction operating configuration, a bacteria disinfection operating configuration, and a condition monitoring operating configuration, wherein each operating configuration includes a unique combination of a target wavelength, a target intensity range, and a target pattern for the ultraviolet radiation;
        monitoring a set of current conditions of at least one of: the storage area or a set of items located in the storage area, wherein the set of current conditions includes a change in visual appearance of at least one of: the storage area or the set of items located in the storage area; and
        controlling ultraviolet radiation generated by the set of ultraviolet radiation sources using a selected one of the plurality of selectable operating configurations and the set of current conditions.

19. The refrigeration device of claim 18, further comprising a set of ultraviolet radiation detectors configured to detect a level of ultraviolet radiation within the storage area, wherein the monitoring and control system processes data corresponding to the level of ultraviolet radiation to determine a presence of at least one of: bacteria or a virus.

20. The refrigeration device of claim 18, wherein at least one ultraviolet radiation source in the set of ultraviolet radiation sources is configured to generate ultraviolet radiation to excite a fluorescence, wherein the monitoring and control system processes data corresponding to a level of fluorescence to determine a presence of at least one of: bacteria or microorganisms.

* * * * *